(12) United States Patent
Yajima et al.

(10) Patent No.: US 7,718,816 B2
(45) Date of Patent: May 18, 2010

(54) CARBOXAMIDE DERIVATIVE, PROCESSES FOR PRODUCING THE SAME, AND DETERGENT COMPOSITION

(75) Inventors: Toshio Yajima, Tokyo (JP); Akiko Kawashima, Tokyo (JP)

(73) Assignee: Lion Akzo Co., Ltd., Yokkaichi-Shi (JP)

( * ) Notice: Subject to any disclaimer, the term of this patent is extended or adjusted under 35 U.S.C. 154(b) by 611 days.

(21) Appl. No.: 11/474,501

(22) Filed: Jun. 26, 2006

(65) Prior Publication Data

US 2007/0010680 A1 Jan. 11, 2007

Related U.S. Application Data

(63) Continuation of application No. PCT/JP2004/019074, filed on Dec. 21, 2004.

(30) Foreign Application Priority Data

Dec. 26, 2003 (JP) .............................. 2003-431978

(51) Int. Cl.
 *C07C 231/02* (2006.01)
(52) U.S. Cl. .......................................... 554/35; 554/36
(58) Field of Classification Search ................... 554/35, 554/36
 See application file for complete search history.

(56) References Cited

FOREIGN PATENT DOCUMENTS

| JP | 6-293620 | 10/1994 |
|----|----------|---------|
| JP | 8-253446 | 10/1996 |
| JP | 9-12521 | 1/1997 |
| JP | 9-316043 | 12/1997 |
| JP | 11-152260 | 6/1999 |
| JP | 11-349542 | 12/1999 |
| JP | 2003-292412 | 10/2003 |

*Primary Examiner*—Shailendra Kumar
(74) *Attorney, Agent, or Firm*—Kratz, Quintos & Hanson, LLP

(57) ABSTRACT

To provide: a carboxamide derivative having reduced content of amide ester; a method for producing thereof; and a detergent composition containing the carboxamide derivative and having excellent low-temperature stability. One method for producing a carboxamide derivative is to react carboxamide, produced with a manufacturing method of carboxamide including 0.02% by weight to 0.18% by weight of amide ester, with hydrogen peroxide, wherein the method includes a carboxamide synthesis process to synthesize carboxamide by reacting diamine with fatty acid ester at a molar rate of 1.20 to 1.60. Another method for producing a carboxamide derivative is to react the carboxamide with monohaloalkylcarboxylic acid or a salt thereof. A carboxamide derivative is produced by the method for producing a carboxamide derivative. A detergent composition includes the carboxamide derivative. The carboxamide derivative is preferably amidoamine oxide or amide betaine.

6 Claims, No Drawings

CARBOXAMIDE DERIVATIVE, PROCESSES FOR PRODUCING THE SAME, AND DETERGENT COMPOSITION

CROSS-REFERENCE TO RELATED APPLICATIONS

This is a continuation to Application No. PCT/JP2004/019074, filed on Dec. 21, 2004.

BACKGROUND OF THE INVENTION

1. Field of the Invention

The present invention relates to: a carboxamide derivative having reduced amide ester content; an efficient production method thereof; and a detergent composition including the carboxamide derivative produced by the production method and having excellent low-temperature stability.

2. Description of the Related Art

Carboxamide is used in a hair conditioner, and it is used as an intermediate of a carboxamide derivative such as amide betaine and amidoamine oxide. In particular, a carboxamide derivative is widely used for cleaning agents such as hair shampoo and dishwashing detergent, cosmetic materials and beauty products since it is less irritating to the skin and has favorable biodegradability.

Carboxamide is usually produced by condensing a fatty acid or an ester thereof with a diamine at a reaction temperature of 80° C. to 200° C. and under a normal or reduced pressure. Also, it is known that an amidoamine oxide as a carboxamide derivative may be obtained by oxidizing carboxamide with hydrogen peroxide, and it is known that amide betaine as a carboxamide derivative may be obtained by reaction of carboxamide with monohaloalkylcarboxylic acid and a salt thereof.

For example, it is considered that the amount of diamine used for the production of highly pure carboxamide is preferably 0.83 times by mole to 1.25 times by mole, and more preferably 1.0 times by mole to 1.2 times by mole, with respect to that of a fatty acid or an ester thereof (paragraph 0017 in Japanese Patent Application Laid-Open (JP-A) No. 11-349542). Also, it is known that an addition of organic phosphonic acid in producing amidoamine oxide yields a composition including amidoamine oxide having superior preservation stability at a high temperature of 50° C. in terms of color and odor (paragraphs 0022 and 0023 in JP-A No. 11-152260).

However, sedimentation occurs during low-temperature preservation of amidoamine oxide, which is obtained by reacting hydrogen peroxide with carboxamide obtained by reacting a fatty acid ester with 1.20 times by mole or less with respect to the fatty acid ester of a diamine, and amino betaine, which is obtained by reacting the carboxamide with a monohaloalkylcarboxylic acid or a salt thereof. This causes problems such as decreased commercial value of amidoamine oxide and amide betaine as well as reduced low-temperature stability of a detergent composition which uses thereof.

SUMMARY OF THE INVENTION

The present invention is aimed at resolving the conventionally existing problems to achieve the following. That is, the present invention is aimed at providing: a carboxamide derivative having reduced amide ester content; an efficient production method thereof; and a detergent composition including the carboxamide derivative produced by the production method and having excellent low-temperature stability.

The inventors of the present invention found out as a result of keen examinations for resolving the problems that the reduced low-temperature stability of a carboxamide derivative was derived from an amide ester included in the carboxamide as a by-product. They also found out that increasing the molar ratio of diamine with respect to fatty acid ester in producing carboxamide by reacting fatty acid ester and diamine could suppress the side reaction of amide ester and produce carboxamide having superior low-temperature stability, and as a result, they accomplished the present invention.

The present invention is based on the findings by the inventors of the present invention, and the means solving the problems are as follows. That is:

<1> A method for producing carboxamide including a process for synthesizing carboxamide, wherein the carboxamide is synthesized by reacting, under no presence of a catalyst, a fatty acid ester represented by General Formula (1) below with a diamine represented by General Formula (2) below at a molar ratio of the diamine to the fatty acid ester of 1.20 to 1.60; and the carboxamide includes 0.02% by weight to 0.18% by weight of amide ester represented by General Formula (3) below:

$R^1$—COOR                General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

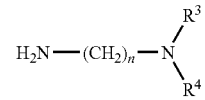

General Formula (2)

wherein, in General Formula (2) above, $R^3$ and $R^4$ are the same or different and represent an alkyl group having a carbon number of one to four; and n represents an integer of two to four; and

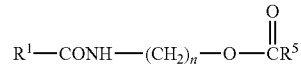

General Formula (3)

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four.

<2> The method for producing carboxamide according to <1>, wherein the reaction temperature in the process for synthesizing carboxamide is 190° C. to 200° C.

<3> A method for producing a carboxamide derivative including a process for producing a carboxamide derivative by reacting carboxamide produced by a method for producing carboxamide and hydrogen peroxide, wherein the carboxamide is synthesized by reacting, under no presence of a catalyst, a fatty acid ester represented by General Formula (1) below with a diamine represented by General Formula (2) below at a molar ratio of the diamine to the fatty acid ester of 1.20 to 1.60;

the carboxamide includes 0.02% by weight to 0.18% by weight of amide ester represented by General Formula (3) below; and the carboxamide derivative is represented by General Formula (4) below:

  General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

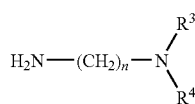  General Formula (2)

wherein, in General Formula (2) above, $R^3$ and $R^4$ are the same or different and represent an alkyl group having a carbon number of one to four; and n represents an integer of two to four;

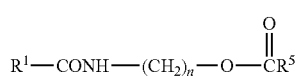  General Formula (3)

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four; and

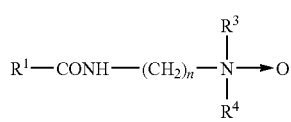  General Formula (4)

wherein, in General Formula (4), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

<4> A method for producing a carboxamide derivative including a process for producing a carboxamide derivative by reacting carboxamide produced by a method for producing carboxamide and any one of monohaloalkylcarboxylic acid represented by Structural Formula (5) below and a salt thereof, wherein the carboxamide is synthesized by reacting, under no presence of a catalyst, a fatty acid ester represented by General Formula (1) below with a diamine represented by General Formula (2) below at a molar ratio of the diamine to the fatty acid ester of 1.20 to 1.60;

the carboxamide includes 0.02% by weight to 0.18% by weight of amide ester represented by General Formula (3) below; and the carboxamide derivative represented by General Formula (6) below:

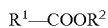  General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

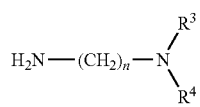  General Formula (2)

wherein, in General Formula (2) above, $R^3$ and $R^4$ are the same or different and represent an alkyl group having a carbon number of one to four; and n represents an integer of two to four;

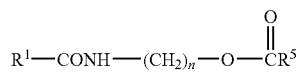  General Formula (3)

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four;

  General Formula (5)

wherein, in General Formula (5), Y represents a halogen atom; $R^6$ represents a straight-chain or branched-chain alkylene group having a carbon number of one to three; and Z represents any one of a hydrogen atom and an alkali metal atom; and

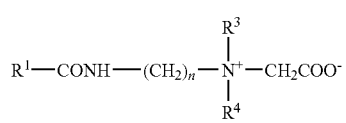  General Formula (6)

wherein, in General Formula (6), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

<5> The method for producing carboxamide according to <3>, wherein the reaction temperature in the process for synthesizing carboxamide is 190° C. to 200° C.

<6> The method for producing carboxamide according to <4>, wherein the reaction temperature in the process for synthesizing carboxamide is 190° C. to 200° C.

<7> The method for producing a carboxamide derivative according to <3>,
wherein the content of amide ester represented by General Formula (3) below in the carboxamide derivative is 0.05% by weight or less:

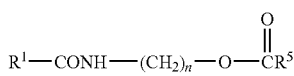

General Formula (3)

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four.

<8> The method for producing a carboxamide derivative according to <4>,
wherein the content of amide ester represented by General Formula (3) below in the carboxamide derivative is 0.05% by weight or less:

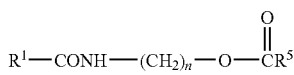

General Formula (3)

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four.

<9> A carboxamide derivative produced by a method for producing a carboxamide derivative,
wherein the method for producing a carboxamide derivative includes a process for producing a carboxamide derivative by reacting carboxamide produced by a method for producing carboxamide and hydrogen peroxide;
the method for producing carboxamide includes a process for synthesizing carboxamide by reacting, under no presence of a catalyst, a fatty acid ester represented by General Formula (1) below with a diamine represented by General Formula (2) below at a molar ratio of the diamine to the fatty acid ester of 1.20 to 1.60;
the carboxamide includes 0.02% by weight to 0.18% by weight of amide ester represented by General Formula (3) below; and
the carboxamide derivative is represented by General Formula (4) below:

R¹—COOR    General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

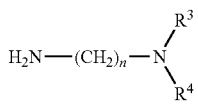

General Formula (2)

wherein, in General Formula (2) above, $R^3$ and $R^4$ are the same or different and represent an alkyl group having a carbon number of one to four; and n represents an integer of two to four;

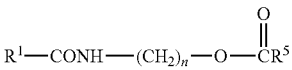

General Formula (3)

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four; and

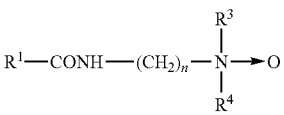

General Formula (4)

wherein, in General Formula (4), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

<10> A carboxamide derivative produced by a method for producing a carboxamide derivative,
wherein the method for producing a carboxamide derivative includes a process for producing a carboxamide derivative by reacting carboxamide produced by a method for producing carboxamide and any one of monohaloalkylcarboxylic acid and a salt thereof,
wherein the method for producing carboxamide includes a process for synthesizing carboxamide by reacting, under no presence of a catalyst, a fatty acid ester represented by General Formula (1) below with a diamine represented by General Formula (2) below at a molar ratio of the diamine to the fatty acid ester of 1.20 to 1.60;
the carboxamide includes 0.02% by weight to 0.18% by weight of amide ester represented by General Formula (3) below; and
the carboxamide derivative is represented by General Formula (6) below:

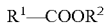

R¹—COOR²    General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

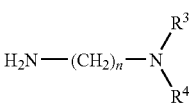

General Formula (2)

wherein, in General Formula (2) above, $R^3$ and $R^4$ are the same or different and represent an alkyl group having a carbon number of one to four; and n represents an integer of two to four;

General Formula (3)

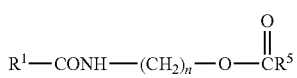

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four;

 General Formula (5)

wherein, in General Formula (5), Y represents a halogen atom; $R^6$ represents a straight-chain or branched-chain alkylene group having a carbon number of one to three; and Z represents any one of a hydrogen atom and an alkali metal atom; and General Formula (6)

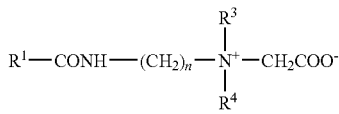

wherein, in General Formula (6), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

<11> The carboxamide derivative according to <9>, wherein the carboxamide derivative is amidoamine oxide.

<12> The carboxamide derivative according to <10>, wherein the carboxamide derivative is amidoamine oxide.

<13> The carboxamide derivative according to <9>, wherein the carboxamide derivative is amide betaine.

<14> The carboxamide derivative according to <10>, wherein the carboxamide derivative is amide betaine.

<15> A detergent composition including a carboxamide derivative,
wherein the carboxamide derivative is produced by a method for producing a carboxamide derivative,
wherein the method for producing a carboxamide derivative includes a process for producing a carboxamide derivative by reacting carboxamide produced by a method for producing carboxamide and hydrogen peroxide,
wherein the method for producing carboxamide includes a process for synthesizing carboxamide by reacting, under no presence of a catalyst, a fatty acid ester represented by General Formula (1) below with a diamine represented by General Formula (2) below at a molar ratio of the diamine to the fatty acid ester of 1.20 to 1.60;
the carboxamide includes 0.02% by weight to 0.18% by weight of amide ester represented by General Formula (3) below; and
the carboxamide derivative is represented by General Formula (4) below:

$R^1$—COOR$^2$  General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

General Formula (2)

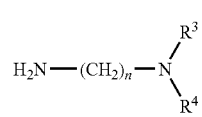

wherein, in General Formula (2) above, $R^3$ and $R^4$ are the same or different and represent an alkyl group having a carbon number of one to four; and n represents an integer of two to four;

General Formula (3)

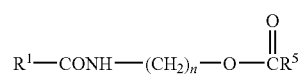

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four; and General Formula (4)

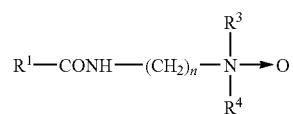

wherein, in General Formula (4), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

<16> A detergent composition including a carboxamide derivative,
wherein the carboxamide derivative is produced by a method for producing a carboxamide derivative;
the method for producing a carboxamide derivative includes a process for producing a carboxamide derivative by reacting carboxamide produced by a method for producing carboxamide and any one of monohaloalkylcarboxylic acid and a salt thereof,
wherein the method for producing carboxamide includes a process for synthesizing carboxamide by reacting, under no presence of a catalyst, a fatty acid ester represented by General Formula (1) below with a diamine represented by General Formula (2) below at a molar ratio of the diamine to the fatty acid ester of 1.20 to 1.60;
the carboxamide includes 0.02% by weight to 0.18% by weight of amide ester represented by General Formula (3) below; and
the carboxamide derivative is represented by General Formula (6) below:

$R^1$—COOR$^2$  General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

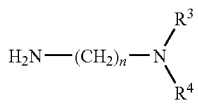
General Formula (2)

wherein, in General Formula (2) above, $R^3$ and $R^4$ are the same or different and represent an alkyl group having a carbon number of one to four; and n represents an integer of two to four;

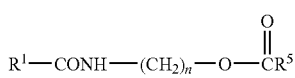
General Formula (3)

wherein, in General Formula (3) above, $R^1$ and $R^5$ represent any one of a straight-chain or branched-chain alkyl group, alkenyl group and hydroxyalkyl group having a carbon number of five to 23; and n represents an integer of two to four;

$YR^6COOZ$      General Formula (5)

wherein, in General Formula (5), Y represents a halogen atom; $R^6$ represents a straight-chain or branched-chain alkylene group having a carbon number of one to three; and Z represents any one of a hydrogen atom and an alkali metal atom; and

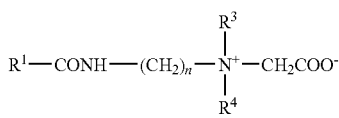
General Formula (6)

wherein, in General Formula (6), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

<17> The detergent composition according to <15>, wherein the reaction temperature in the process for synthesizing carboxamide is 190° C. to 200° C.

<18> The detergent composition according to <16>, wherein the reaction temperature in the process for synthesizing carboxamide is 190° C. to 200° C.

<19> The detergent composition according to <15>, wherein the carboxamide derivative is any one of amidoamine oxide and amide betaine.

<20> The detergent composition according to <16>, wherein the carboxamide derivative is any one of amidoamine oxide and amide betaine.

DESCRIPTION OF THE PREFERRED EMBODIMENTS

Method for Producing Carboxamide

A method for producing carboxamide of the present invention includes a process for synthesizing carboxamide, and it further includes other processes according to requirements.

<Carboxamide Synthesis Process>

The process for synthesizing carboxamide is to synthesize carboxamide through a reaction of fatty acid ester with diamine.

—Fatty Acid Ester—

Examples of the fatty acid ester include fatty acid esters represented by General Formula (1) below:

$R^1$—$COOR^2$      General Formula (1)

where, in General Formula (1) above, $R^1$ represents any one of a straight-chain or branched-chain alkyl group, alkenyl group and hydroxyalkyl group having a carbon number of five to 23; and $R^2$ represents a straight-chain or branched-chain alkyl group having a carbon number of one to four.

The fatty acid esters are not particularly restricted and can be appropriately selected according to applications, and examples thereof include: methyl ester, ethyl ester or glyceride of vegetable oil or animal oil fatty acid, and a mixture thereof. Among these, a higher fatty acid with the $R^2$ as an alkyl group having a carbon number of one to four and a lower alkyl ester thereof are preferable, and ones with the $R^1$ as a straight-chain alkyl group having a carbon number of nine to 21 and the $R^2$ as a methyl group are particularly preferable.

The vegetable oil or animal oil fatty acid is not particularly restricted and can be appropriately selected according to applications. Examples thereof include: caprylic acid, capric acid, lauric acid, myristic acid, palmitic acid, stearic acid, oleic acid, behenic acid, erucic acid, 12-hydroxystearic acid, coconut oil fatty acid, cotton seed oil fatty acid, corn oil fatty acid, tallowate, babassu oil fatty acid, palm kernel oil fatty acid, soybean oil fatty acid, linseed oil fatty acid, castor oil fatty acid, olive oil fatty acid, blubber oil fatty acid and palm oil fatty acid.

—Diamine—

Examples of the diamine include diamines represented by General Formula (2) below:

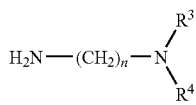
General Formula (2)

where, in General Formula (2) above, $R^3$ and $R^4$ are the same or different and represent an alkyl group having a carbon number of one to four; and n represents an integer of two to four.

The diamines are not particularly restricted and can be appropriately selected according to applications. Examples thereof include dimethylaminopropylamine, dimethylaminoethylamine, diethylaminopropylamine, diethylaminoethylamine, dibutylaminopropylamine, dibutylaminoethylamine, dipropylaminopropylamine and dipropylaminoethylamine. Among these, dimethylaminopropylamine and diethylaminoethylamine are favorably used.

In the carboxamide synthesis process, the reaction temperature is preferably 80° C. to 220° C., more preferably 100° C. to 200° C., and further more preferably 160° C. to 200° C. The reaction time is preferably three hours to 20 hours, and more preferably five hours to 10 hours.

In the carboxamide synthesis process, the molar ratio of the diamine with respect to the fatty acid ester is preferably 1.20 to 1.60, and more preferably 1.25 to 1.40.

When the molar ratio exceeds 1.60, the reflux rate of the diamine during reaction increases considerably, and the reaction temperature cannot be maintained at 160° C. to 200° C., which may slow down the reaction. In addition, the concentration of the active ingredients becomes low, and the productivity may be reduced. When the molar ratio is less than 1.20, the content of amide ester produced as a by-product during the reaction increases, and it may adversely affect the low-temperature stability of the carboxamide mentioned hereinafter.

Here, the productivity of carboxamide may be obtained by the following equation: productivity (g/(g·h))=solid content concentration (% by weight)/time required to reach the conversion of 99.5% (h).

The diamine may be charged at the initial stage of the reaction, or it may be delivered by drops from the gas phase or introduced in the reacting solution during the reaction. Also, in order to suppress the distillation of reacting diamine, the diamine may be charged such that the molar ratio of the diamine with respect to the ester is 0.3 to 1.0 and reacted at a temperature of 150° C. to 170° C., and then with the rest of the diamine delivered by drops, the system may be heated to a temperature of 170° C. to 220° C. and aged until the quantity of unreacted diamine is reduced.

The carboxamide synthesis process may take place under a reduced pressure, at a normal pressure or under increased pressure.

The carboxamide synthesis process may take place under the presence of alkali catalyst such as sodium methoxide. The presence of the alkali catalyst may decrease the reaction temperature or shorten the reaction time.

In the above process, the fatty acid ester and the diamine react to produce carboxamide.

<Other Processes>

The other processes are not particularly restricted and can be appropriately selected according to applications. Favorable examples thereof include a distillation process and a recovery process.

The distillation process is a process to distill off a lower alcohol produced as a by-product in the carboxamide synthesis process.

A method for the distillation is not particularly restricted and can be appropriately selected from heretofore known methods according to applications. For example, in the carboxamide synthesis process, the temperature may be controlled above the boiling point of the lower alcohol and below the boiling point of the diamine by means of a condenser. Here, it is preferable to blow an inert gas such as nitrogen gas in view of promoting the distillation.

In the above process, the lower alcohol is distilled from the reacting solution.

The recovery process is a process to distill and recover the unreacted diamine after the completion of the carboxamide synthesis process. The diamine recovered in the recovery process may be reused in the carboxamide synthesis process.

A method for the recovery is not particularly restricted and can be appropriately selected from heretofore known methods according to applications. For example, the recovery may be performed under a reduced pressure or with nitrogen blow down method.

In the above process, the unreacted diamine may be recovered from the reacting solution.

As the other process, by distilling only the lower alcohol and refluxing the unreacted diamine, the carboxamide may be efficiently produced in the carboxamide synthesis process.

(Carboxamide)

Carboxamide of the present invention is produced by means of the method for producing carboxamide of the present invention. The carboxamide includes an amide ester as a by-product.

Specific examples of the carboxamide include: decanoic acid dimethylaminopropylamide, decanoic acid dimethylaminoethylamide, decanoic acid diethylaminoethylamide, decanoic acid diethylaminopropylamide, decanoic acid dibutylaminopropylamide, lauric acid dimethylaminopropylamide, lauric acid dimethylaminoethylamide, lauric acid diethylaminoethylamide, lauric acid diethylaminopropylamide, lauric acid dibutylaminopropylamide, myristic acid dimethylaminopropylamide, myristic acid dimethylaminoethylamide, myristic acid diethylaminoethylamide, myristic acid diethylaminopropylamide, myristic acid dibutylaminopropylamide, palmitic acid dimethylaminopropylamide, palmitic acid dimethylaminoethylamide, palmitic acid diethylaminoethylamide, palmitic acid diethylaminopropylamide, palmitic acid dibutylaminopropylamide, stearic acid dimethylaminopropylamide, stearic acid dimethylaminoethylamide, stearic acid diethylaminoethylamide, stearic acid diethylaminopropylamide, stearic acid dibutylaminopropylamide, oleic acid dimethylaminopropylamide, oleic acid dimethylaminoethylamide, oleic acid diethylaminoethylamide, oleic acid diethylaminopropylamide, oleic acid dibutylaminopropylamide, coconut oil fatty acid dimethylaminopropylamide, coconut oil fatty acid dimethylaminoethylamide, coconut oil fatty acid diethylaminoethylamide, coconut oil fatty acid diethylaminopropylamide, coconut oil fatty acid dibutylaminopropylamide, hardened tallow dimethylaminopropylamide, hardened tallow dimethylaminoethylamide, hardened tallow diethylaminoethylamide, hardened tallow diethylaminopropylamide, hardened tallow dibutylaminopropylamide, behenic acid dimethylaminopropylamide, behenic acid dimethylaminoethylamide, behenic acid diethylaminoethylamide, behenic acid diethylaminopropylamide, behenic acid dibutylaminopropylamide, isostearic acid dimethylaminopropylamide, isostearic acid dimethylaminoethylamide, isostearic acid diethylaminoethylamide, isostearic acid diethylaminopropylamide and isostearic acid dibutylaminopropylamide, The carboxamide may be stored as a solid at a room temperature or as a liquid after heating. It is preferably sealed with nitrogen to suppress the color degradation.

Examples of the amide ester include amide esters represented by General Formula (3) below:

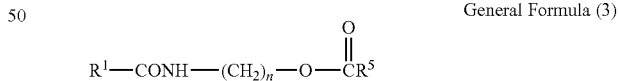

General Formula (3)

where, in General Formula (3), $R^1$ and $R^5$ represent any one of a straight-chain or branched-chain alkyl group, alkenyl group and hydroxyalkyl group having a carbon number of five to 23; and n represents an integer of two to four.

Specific examples of the amide esters include amide esters represented by General Formulae (7) to (13):

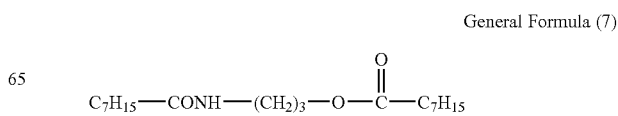

General Formula (7)

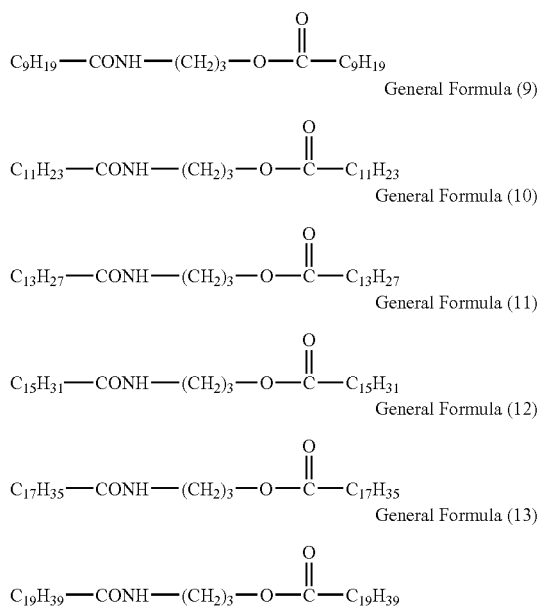

-continued

General Formula (8)

General Formula (9)

General Formula (10)

General Formula (11)

General Formula (12)

General Formula (13)

The content of the amide ester in the carboxamide is preferably 0.02% by weight to 0.18% by weight. The increased content thereof may adversely affect the low-temperature stability of the carboxamide derivative mentioned hereinafter.

When a mixture of the fatty acid esters is used as the fatty acid ester, the alkyl chain length of the amide ester is not a single chain but a mixture of the alkyl chain lengths of the used fatty acid esters.

(Method for Producing Carboxamide Derivative)

A method for producing a carboxamide derivative of the present invention is performed through a reaction of the carboxamide and hydrogen peroxide.

The method for reacting the carboxamide and hydrogen peroxide is not particularly restricted and can be appropriately selected from heretofore known methods according to applications.

It is preferable that the hydrogen peroxide is dissolved in a solvent and used as a solution, and it is more preferable that the solution is an aqueous solution.

Preferable examples of the solvent include one or more types of solvents selected at least from water and alcohols.

The alcohols are not particularly restricted and can be appropriately selected according to applications. Examples thereof include ethanol, 2-propanol and propylene glycol. Among these, 2-propanol and ethanol may be favorably used since they can increase the concentration of the active ingredient concentration of a generated carboxamide derivative.

The amount of the solvent used is not particularly restricted as long as it is sufficient for agitating and mixing the reaction products; it may be appropriately selected according to applications. Since the active ingredient concentration of the carboxamide derivative in a reaction product is preferably 10% by weight to 50% by weight, and more preferably 15% by weight to 40% by weight, it is preferable that the amount of the solvent used suffices the active ingredient concentration. When the amount used is too small, the mixed state of the reaction products is impaired, and the mixture may turn into a gel. When the amount used is too large, the concentration of the carboxamide derivative decreases and the productivity may be reduced.

The molar ratio of the hydrogen peroxide to the carboxamide is preferably 0.9 to 1.4, more preferably 1.0 to 1.3, and further more preferably 1.02 to 1.10. The small molar ratio of hydrogen peroxide increases the reaction time as well as the carboxamide content, and the large molar ratio of hydrogen peroxide increases the amount of remaining hydrogen peroxide after reaction and tends to cause side reaction. Therefore, too small or too large molar ratio of hydrogen peroxide is not preferable.

The hydrogen peroxide concentration in the hydrogen peroxide solution is preferably 5% by weight to 60% by weight, and more preferably 8% by weight to 45% by weight. When the hydrogen peroxide concentration is too high, self-decomposition of the hydrogen peroxide as well as a local reaction may occur. On the other hand, when the hydrogen peroxide concentration is too small, the carboxamide concentration with respect to the solvent is too high, impairing the fluidity and possibly reducing the productivity. It is preferable that the charged amount of the hydrogen peroxide solution suffices the molar ratio. Also, the carboxamide and the hydrogen peroxide solution may be replenished during the reaction.

After the charge of hydrogen peroxide, the agitation state is preferably maintained in order to enhance the conversion of the carboxamide.

The temperature during the charge of hydrogen peroxide and agitation is preferably maintained above the temperature at which the reactants may be agitated and mixed as well as at or below the decomposition temperature of the carboxamide derivative. Such temperature is, for example, preferably 50° C. to 100° C., and more preferably 80° C. to 90° C. Also, the agitation is maintained, for example, preferably for 30 minutes to 24 hours, and more preferably one hour to eight hours.

The carboxamide and the hydrogen peroxide may be reacted under an increased pressure or a normal pressure.

Also, when a large amount of the hydrogen peroxide has remained unreacted in the reaction product after the completion of the reaction, the carboxamide may be added, or a decomposition reaction selected from heretofore known methods may be performed according to requirements. Examples of the decomposition reaction methods include a method to add sodium hydroxide.

Also, a method for producing a carboxamide derivative of the present invention may be performed by reacting the carboxamide and any one of monohaloalkylcarboxylic acid represented by General Formula (5) below and a salt thereof:

$$YR^6COOZ \qquad \text{General Formula (5)}$$

where, in General Formula (5), Y represents a halogen atom; $R^6$ represents a straight-chain or branched-chain alkylene group having a carbon number of one to three; and Z represents any one of a hydrogen atom and an alkali metal atom.

The method for reacting carboxamide and any one of monohaloalkkylcarboxylic acid and a salt thereof is not particularly restricted and can be appropriately selected from heretofore known methods according to applications. Examples thereof include a method to mix the carboxamide and any one of the monohaloalkylcarboxylic acid and the salt thereof with water for reaction. Here, the reaction is preferably performed at a pH maintained in the range of 8 to 13 by means of an alkali such as sodium hydroxide. Also, the reaction temperature is preferably set in the range of 50° C. to 100° C. The reaction may be performed under an increased pressure or a normal pressure.

The monohaloalkkylcarboxylic acid and the salt thereof is preferably dissolved in a solvent and used as a solution, and the solution is more preferably an aqueous solution.

Preferable examples of the solvent include one or more types of solvents selected at least from water and alcohols.

The alcohols are not particularly restricted and can be appropriately selected according to applications. Examples thereof include ethanol, 2-propanol and propylene glycol.

The monohaloalkylcarboxylic acid and the salt thereof are not particularly restricted and can be appropriately selected according to applications. Examples thereof include monochloroacetic acid, monobromoacetic acid, monochloropropionic acid, monobromopropionic acid, sodium salts thereof and potassium salts thereof. Among these, monochloroacetic acid and salts thereof are particularly preferable.

The molar ratio of the monohaloalkylcarboxylic acid or the salt thereof with respect to the carboxamide is preferably 1 to 1.3, and more preferably 1 to 1.15.

(Carboxamide Derivative)

A carboxamide derivative of the present invention may be produced by means of the method for producing a carboxamide derivative of the present invention.

Favorable examples of the carboxamide derivative include: amidoamine oxides represented by General Formula (4), which may be produced by reacting the carboxamide and the hydrogen peroxide; and amide betaines represented by General Formula (6), which may be produced by reacting the carboxamide with any one of the monohaloalkylcarboxylic acid and the salt thereof.

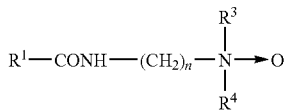

General Formula (4)

where, in General Formula (4), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

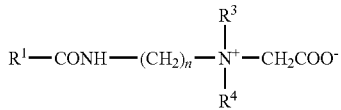

General Formula (6)

where, in General Formula (6), $R^1$ represents any one of a straight-chain or branched-chain alkyl group, alkenyl group and hydroxyalkyl group having a carbon number of five to 23; $R^3$ and $R^4$ are the same or different, representing an alkyl group having a carbon number of one to four; and n represents an integer of two to four.

Examples of the carboxamide derivative other than the amidoamine oxides and the amide betaines include a quaternary salt of amide and amide carboxylate.

The carboxamide derivative includes amide ester represented by General Formula (3) above as a by-product. The content of the amide ester in the carboxamide derivative is preferred to be as small as possible, and more specifically, it is preferably 0.05% by weight or less.

When the content exceeds 0.05% by weight, the amide ester cannot be solubilized and precipitates in the solution which includes the carboxamide derivative, and the solution may become clouded with the precipitation. As for lauric acid amide propyl lauryl ester, though it depends on the chain length, the precipitation of the amide ester does not dissolve until it is heated to 30° C. or higher, and especially during winter, the solution becomes cloudy during preservation due to precipitation unless it is heated and stored. When the content is 0.05% by weight or less, the carboxamide derivative having superior low-temperature stability with no precipitation during preservation at a low temperature of, for example, 0° C. may be obtained.

The carboxamide derivative produced by means of a method for producing a carboxamide derivative of the present invention and using carboxamide produced with the method for producing carboxamide of the present invention yields a reduced content of the amide ester and superior low-temperature stability. Therefore, it may be favorably used for a detergent composition of the present invention described below.

(Detergent Composition)

A detergent composition of the present invention includes the carboxamide derivative produced by means of the method for producing a carboxamide derivative of the present invention, and it further includes other components according to requirements.

Favorable examples of the carboxamide derivative included in the detergent composition include the amidoamine oxides and the amide betaines of the present invention.

The other components are not particularly restricted and appropriately selected from heretofore known components which have conventionally been used for a detergent composition according to applications. Examples thereof include anionic surfactants, non-ionic surfactants and amphoteric surfactants.

The anionic surfactants are not particularly restricted and can be appropriately selected according to applications. Examples thereof include polyoxyethylene alkyl sulfates, alkylbenzene sulfonates, alkyl sulfates, α-olefin sulfonates, alkyl ether carboxylates, alkane sulfonates, α-sulfo fatty acid salts, soaps, amide ether carboxylates, sulfo succinates, fatty acid salts, acyl glutamates, acyl sarcosinates, N-methyl-β-alanine salts and acyl-methyl taurates.

The non-ionic surfactants are not particularly restricted and can be appropriately selected according to applications. Examples thereof include: polyoxyethylene alkyl ethers such as polyoxyethylene(12) lauryl ether, polyoxyethylene(12) decyl ether, polyoxyethylene(15) lauryl ether, polyoxyethylene(15) myristyl ether, polyoxyethylene(20) lauryl ether, polyoxyethylene(20) myristyl ether and polyoxyethylene (30) lauryl ether; alkyl polyglycosides; alkanolamides such as capric acid monoethanolamide, capric acid diethanolamide, lauric acid monoethanolamide, lauric acid diethanolamide, myristic acid monoethanolamide, myristic acid diethanolamide, coconut fatty acid monoethanolamide and coconut fatty acid diethanolamide; polyoxyethylene monoethanolamides such as polyoxyethylene(2) lauric acid monoethanolamide; N-methylglucamide ester; and alkyl amine oxide.

The amphoteric surfactants are not particularly restricted and can be appropriately selected according to applications. Examples thereof include: alkylamino betaines, alkyl acetic acid betaines, alkyl hydroxysulfobetaines, alkyl imidazolinium-betaines and alkyl aminopropionic acid. The other components include: high-polymer silicone compounds; organic acids or salts thereof such as citric acid, malic acid and lactic acid; amino acids such as glutamic acid, glycine and alanine; anionic polymers; cationic polymers, amphoteric polymers; non-ionic polymers; disinfectants; higher alcohols, hydrocarbons; fats, oils, esters and antioxidants; metal sequestrants; colorants; flavors; solvents such as ethanol and carbitol derivative; polyols; and fatty acids. These other components may be used alone or in combination of two or more types.

A detergent composition of the present invention includes the carboxamide derivative with low content of the amide ester of the present invention, and it has favorable low-temperature stability as well as superior detergency and foaming power. Therefore, it may be favorably used for various kinds of detergents, especially hair shampoo, body shampoo, face wash, hair treatment, dishwashing detergent and various household detergents.

The present invention is illustrated in detail with reference to examples given below, but these are not to be construed as limiting the present invention.

Example 1

Preparation of Carboxamide

—Carboxamide Synthesis Process—

In a 1-Liter four-neck flask equipped with a stirrer, a thermometer and a reflux condenser, 352 g of lauric acid methyl ester (PASTELL M-12 having a molecular weight of 214, manufactured by Lion Chemical Co., Ltd.) was charged, and the flask was purged twice with nitrogen (returning from a reduced pressure of 6.7 kPa to a normal pressure with nitrogen). Next, it was heated to 180° C., and 202 g of N,N-dimethyl-1,3-propanediamine (hereinafter referred to as DMAPA) of which the molar ratio with respect to lauric acid methyl ester was 1.20 was delivered by drops at 190° C. to 200° C. for four hours. Then, it was aged at 190° C. to 200° C. for five hours, and carboxamide was obtained. The said carboxamide was lauric acid dimethylaminopropylamide.

—Distillation Process and Recovery Process—

Hot water at a temperature of 80° C. was run through the reflux condenser, and methanol as a by-product in the carboxamide synthesis process was distilled off. Also, unreacted DMAPA was recovered through partial condensation and returned to the reactor.

—Measurement of Conversion of Fatty Acid Ester to Carboxamide—

The amount of unreacted lauric acid methyl ester was measured with a gas chromatographic (GC) analysis based on the following GC conditions, and the conversion of lauric acid methyl ester to carboxamide was calculated. The time required for the conversion to reach 99.5% was 6.2 hours.

[GC Conditions]

HP-5860 (manufactured by Agilent Technologies, Inc.) was used as a gas chromatographic apparatus, and DB-17 (0.25 mm in diameter×30 m in length, with a film thickness of 0.25 μm and manufactured by J & W) was used as a column. The column temperature was initially 60° C. and increased at a rate of 5° C./min until it reached 280° C. Then, the system was maintained at 280° C. for 40 minutes. The injection temperature was 280° C.; the detector temperature was 280° C.; the carrier gas was helium; the split ratio was 1:10, the detector was FID; the sample concentration was 2% by weight (2-propanol); and the injection amount was 1 μL.

—Measurement of Solid Concentration—

The solid concentration of the reaction mixture was measured based on the following solid content analysis conditions. The solid concentration was 93.5% by weight.

[Solid Content Analysis Conditions]

PD 600 (manufactured by Kett Electric Laboratory) was used for the apparatus, and the analysis was performed at a temperature of 105° C. for 60 minutes. The sample quantity was 2 g. Also, the amount of the solid content was calculated by: solid content (% by weight)=100−volatile content (% by weight).

—Measurement of Amide Ester Quantity—

The reaction mixture was depressurized to 2.0 kPa at 190° C. and topped for one hour to remove unreacted DMAPA. Next, it was cooled to 90° C. to recover the reaction mixture. The amide ester content in this reaction mixture was calculated with GC-MS analysis based on the following GC-MS analysis conditions. Here, the amide ester develops its peak on the GC chromatogram at 54.3 minutes after the peaks of methyl laurate (18.2 minutes) and $C_{12}$ carboxamide (35.1 minutes). The content of amide ester ($C_{11}H_{23}CONH(CH_2)_3OCOC_{11}H_{23}$, having a molecular weight of 439) was 0.18% by weight (GC area %).

[GC-MS Analysis Conditions]

HP-6890/5972 (manufactured by Agilent Technologies, Inc.) was used as a gas chromatographic apparatus, and DB-17 (0.25 mm in diameter×30 m in length, with a film thickness of 0.25 μm, manufactured by J & W) was used as a column. The column temperature was initially 60° C. and increased at a rate of 5° C./min until it reached 280° C. Then, the system was maintained at 280° C. for 40 minutes. The injection temperature was 280° C.; the detector temperature was 280° C.; helium was injected as a carrier gas at a rate of 1.0 mL/min; the EI method was adopted as an ionization method; and the ionization voltage was 70 eV. The split ratio was 1:10; the sample concentration was 2% by weight (2-propanol); and the injection amount was 1 μL.

Example 2

Preparation of Carboxamide

Carboxamide was produced in the same manner as Example 1 except that 340 g of lauric acid methyl ester and 211 g of N,N-dimethyl-1,3-propanediamine (DMAPA) were used at a molar ratio of DMAPA to lauric acid methyl ether of 1.30. The said carboxamide was lauric acid dimethylaminopropylamide.

To lauric acid methyl ester, DMAPA was delivered by drops at 190° C. to 195° C. for four hours. Then, it was aged at 190° C. to 195° C. for three hours. Unreacted methyl ester was measured periodically, and the time to 99.5-% conversion was found to be 6.1 hours. The solid concentration in the reaction mixture was 90.5% by weight. Then, the reaction mixture was depressurized and topped in the same manner as Example 1 to recover the reaction product. The amide ester content in the reaction product was analyzed with gas chromatography, and it was found to be 0.05% by weight.

Example 3

Preparation of Carboxamide

Carboxamide was produced in the same manner as Example 1 except that 237 g of lauric acid methyl ester and 310 g of N,N-dimethyl-1,3-propanediamine (DMAPA) were used at a molar ratio of DMAPA to lauric acid methyl ester of 1.60. The said carboxamide was lauric acid dimethylaminopropylamide.

DMAPA was delivered by drops to lauric acid methyl ester at 190° C. to 195° C. for four hours. When DMAPA was delivered by drops and the reflux amount of the unreacted DMAPA increased, much of the heat supplied to the reaction mixture was used for vaporization of DMAPA. Therefore, the temperature could not reach over 170° C. Next, the system was aged at 170° C. for two hours. Unreacted lauric acid methyl ester was measured periodically, and the time to 99.5-% conversion was found to be 5.3 hours. The solid concentration in the reaction mixture was 82.4% by weight. Then, the reaction mixture was depressurized and topped in the same manner as Example 1 to recover the reaction product. The amide ester content in the reaction product was analyzed with gas chromatography, and it was found to be 0.02% by weight.

Example 4

Preparation of Carboxamide

Carboxamide was produced in the same manner as Example 1 except that 222 g of capric acid methyl ester and 337 g of N,N-dimethyl-1,3-propanediamine (DMAPA) were used at a molar ratio of DMAPA to capric acid methyl ether of 1.20. The said carboxamide was capric acid dimethylaminopropylamide.

DMAPA was delivered by drops to capric acid methyl ester at 190° C. to 200° C. for four hours, and the system was aged for four hours. Unreacted methyl ester was measured periodically, and the time to 99.5-% conversion was found to be 6.2 hours. The solid concentration in the reaction mixture was 92.8% by weight. Then, the reaction mixture was depressurized and topped in the same manner as Example 1 to recover the reaction product. The amide ester content in the reaction product was analyzed with gas chromatography, and it was found to be 0.15% by weight.

Comparative Example 1

Preparation of Carboxamide

Carboxamide was produced in the same manner as Example 1 except that 364 g of lauric acid methyl ester and 191 g of N,N-dimethyl-1,3-propanediamine (DMAPA) were used at a molar ratio of DMAPA to lauric acid methyl ether of 1.10. The said carboxamide was lauric acid dimethylaminopropylamide.

DMAPA was delivered by drops to lauric acid methyl ester at 190° C. to 200° C. for four hours, and the system was aged for four hours. Unreacted methyl ester was measured periodically, and the time to 99.5-% conversion was found to be 7.8 hours. The solid concentration in the reaction mixture was 96.7% by weight. Then, the reaction mixture was depressurized and topped in the same manner as Example 1 to recover the reaction product. The amide ester content in the reaction product was analyzed with gas chromatography, and it was found to be 0.4% by weight.

Comparative Example 2

Preparation of Carboxamide

Carboxamide was produced in the same manner as Example 1 except that 293 g of lauric acid methyl ester and 238 g of N,N-dimethyl-1,3-propanediamine (DMAPA) were used at a molar ratio of DMAPA to lauric acid methyl ether of 1.70. The carboxamide was lauric acid dimethylaminopropylamide.

DMAPA was delivered by drops to lauric acid methyl ester for four hours. During this operation, the unreacted DMAPA quantity increased, and the reflux amount of DMAPA increased as well. Since much of the heat supplied to the reaction mixture was used for vaporization of DMAPA, the temperature could not reach over 160° C. at the end of the delivery of DMAPA. While the system was aged for four hours, unreacted methyl ester was measured periodically, and the time to 99.5-% conversion was found to be 6.2 hours. The solid concentration in the reaction mixture was 80.1% by weight. Then, the reaction mixture was depressurized and topped in the same manner as Example 1 to recover the reaction product. The amide ester content in the reaction product was analyzed with gas chromatography, and it was found to be 0.02% by weight.

The measurement results of Examples 1 to 4 and Comparative Examples 1 to 2 are shown in Table 1.

Also for Examples 1 to 4 and Comparative Examples 1 to 2, the productivity of carboxamide was calculated based on the following equation: productivity $(g/(g \cdot h))$=solid content concentration (% by weight)/time required to reach the conversion of 99.5% (h).

TABLE 1

|  | Example 1 | Example 2 | Example 3 | Example 4 | Comparative Example 1 | Comparative Example 2 |
| --- | --- | --- | --- | --- | --- | --- |
| Diamine | DMAPA | DMAPA | DMAPA | DMAPA | DMAPA | DMAPA |
| Fatty acid ester | Methyl laurate | Methyl laurate | Methyl laurate | Methyl caprate | Methyl laurate | Methyl laurate |
| Diamine/fatty acid ester (molar ratio) | 1.20 | 1.30 | 1.60 | 1.20 | 1.10 | 1.70 |
| Time to 99.5-% conversion(h) | 6.2 | 6.1 | 5.3 | 6.2 | 7.8 | 6.2 |
| Solid concentration (% by weight) | 93.5 | 90.5 | 82.4 | 92.8 | 96.7 | 80.1 |
| Productivity $(g/(g \cdot h))$ | 15.1 | 14.8 | 15.5 | 15.0 | 12.4 | 12.9 |
| Amide ester content (% by weight (GC %)) | 0.18 | 0.05 | 0.02 | 0.15 | 0.40 | 0.02 |

In Table 1, DMAPA represents N,N-dimethyl-1,3-propanediamine.

The results in Table 1 indicate the decrease in the amide ester as a by-product with increasing molar ratio of diamine with respect to fatty acid ester, and it was found that carboxamide with low content of amide ester, i.e. 0.02% by weight to 0.18% by weight, could be obtained when the reaction was performed with the molar ratio of diamine with respect to diamine of 1.20 to 1.60. In addition, it was found that carboxamide could be efficiently obtained in Examples 1 to 4 with higher productivity than Comparative Examples 1 to 2.

Regarding Comparative Example 2, the amide ester content of 0.02% by weight was observed when the molar ratio of diamine with respect to fatty acid ester was 1.70. However, the unreacted DMAPA as well as the reflux of DMAPA increased in the carboxamide synthesis process, resulting in the significantly inferior productivity. Thus, it was found that the preferable molar ratio was 1.20 to 1.60.

Example 5

Preparation of Carboxamide Derivative

In a 1-Liter four-neck flask equipped with a stirrer, a thermometer and a reflux condenser, 200 g of lauric acid dimethylaminopropylamide produced in Example 1 (molecular weight calculated based on the amine value of 285, and amide ester quantity of 0.18% by weight) as carboxamide and 345 g of purified water were charged such that the active ingredients accounted for 30% by weight. Next, a commercial product of 45-% by weight hydrogen peroxide was diluted with purified water to 15.6% by weight, and while the mixture was being stirred, 200 g of the prepared hydrogen peroxide (molar ratio with respect to amine of 1.05) was delivered by drops at 75° C. for two hours. After the delivery was completed, the system was aged at 85° C. for five hours, and a reaction product including amidoamine oxide as a carboxamide derivative was obtained.

The quantity of the unreacted lauric acid dimethyl aminopropylamide in the obtained reaction product was measured with HPLC based on the following HPLC analysis conditions. The unreacted carboxamide content was found to be 0.15% by weight.

[HPLC Analysis Conditions]

A differential refractometer (RI) detector and a UV detector were used as detectors, and Capcell Pak SCX UG80 (4.6 mm in diameter×150 m in length, with a film thickness of 5 μm, manufactured by Shiseido Co., Ltd.) was used as a column. A mobile cell was an aqueous methanol solution having a ratio of MeOH to water of 8 to 2, including 0.2% by weight of $NaClO_4$ and 0.2% by weight of $ClCH_2COOH$; the column temperature was 40° C.; the flow rate was 0.75 mL/min; and the injection amount was 10 μL.

Also, the active ingredient concentration (concentration of amidoamine oxide in the reaction product) was analyzed by means of a potentiometric titration using a solution of N/5 hydrochloric acid in 2-propanol and found to be 30.2% by weight. Furthermore, a GC analysis was performed in the same manner as Example 1 to measure the amide ester in the 30-% by weight amidoamine oxide, and it was found to be 0.05% by weight.

Example 6

Preparation of Carboxamide Derivative

A reaction product including amidoamine oxide as a carboxamide derivative was obtained in the same manner as Example 5 except that 200 g of lauric acid dimethylaminopropylamide produced in Example 3 (molecular weight of 285, calculated based on the amine value, and amide ester quantity of 0.02% by weight) was used and that 300 g of purified water and 103 g of 24.3-% by weight of hydrogen peroxide were used in Example 5.

The concentration of the unreacted lauric acid dimethylaminopropylamide in the obtained reaction product was 0.24% by weight. Also, the active ingredient concentration (concentration of amidoamine oxide in the reaction product) was 35.3% by weight. Furthermore, a GC analysis was performed in the same manner as Example 1 to measure the amide ester content in 35-% solution of amidoamine oxide, and it was found to be 0.006% by weight.

Example 7

Preparation of Carboxamide Derivative

A reaction product including amidoamine oxide as a carboxamide derivative was obtained in the same manner as Example 5 except that 200 g of capric acid dimethylaminopropylamide produced in Example 4 (molecular weight calculated of 256, based on the amine value, and amide ester quantity of 0.15% by weight) was used and that 146 g of purified water and 103 g of 24.3-% by weight of hydrogen peroxide were used.

The concentration of the unreacted capric acid dimethylaminopropylamide in the obtained reaction product was 0.26% by weight. Also, the active ingredient concentration (concentration of amidoamine oxide in the reaction product) was 39.8% by weight. Furthermore, a GC analysis was performed in the same manner as Example 1 to measure the amide ester content in 40-% solution of amidoamine oxide, and it was found to be 0.04% by weight.

Comparative Example 3

Preparation of Carboxamide Derivative

A reaction product including amidoamine oxide as a carboxamide derivative was obtained in the same manner as Example 5 except that 200 g of lauric acid dimethylaminopropylamide produced in Comparative Example 1 (molecular weight of 285, calculated based on the amine value, and amide ester quantity of 0.40% by weight) was used and that 345 g of purified water and 200 g of 15.6-% by weight of hydrogen peroxide were used in Example 5.

The concentration of the unreacted lauric acid dimethylaminopropylamide in the obtained reaction product was 0.14% by weight. Also, the active ingredient concentration (concentration of amidoamine oxide in the reaction product) was 30.1% by weight. Furthermore, a GC analysis was performed in the same manner as Example 1 to measure the amide ester content in 40-% solution of amidoamine oxide, and it was found to be 0.11% by weight.

Comparative Example 4

Preparation of Carboxamide Derivative

A reaction product including amidoamine oxide as a carboxamide derivative was obtained in the same manner as Example 5 except that 100 g of lauric acid dimethylaminopropylamide produced in Comparative Example 1 was used and that 504 g of purified water and 100 g of 15.6-% by weight of hydrogen peroxide were used in Example 5.

The concentration of the unreacted lauric acid dimethylaminopropylamide in the obtained reaction product was 0.09% by weight. Also, the active ingredient concentration (concentration of amidoamine oxide in the reaction product) was 15.1% by weight. Furthermore, a GC analysis was performed in the same manner as Example 1 to measure the amide ester content in 15-% solution of amidoamine oxide, and it was found to be 0.06% by weight.

The measurement results of Examples 5 to 7 and Comparative Examples 3 to 4 are shown in Table 2.

Also, the amidoamine oxides produced as a carboxamide derivative in Examples 5 to 7 and Comparative Examples 3 to 4 were preserved at 0° C. for one week, and the low-temperature stability after preservation was evaluated. The appearance of amidoamine oxide was visually observed for its transparency, and the low-temperature stability was rated as 'Good' or 'NG'. The results are shown in Table 2.

amide ester quantity of 0.18% by weight) as carboxamide, 399 g of purified water, 66 g of sodium monochloroacetate (manufactured by Kanto Chemical Co., Inc.; molecular weight of 116.5) and 2.7 g of 30-% by weight sodium hydroxide (manufactured by Kanto Chemical Co., Inc.) were charged such that the active ingredients accounted for 30% by weight. Next, the system was aged at 85° C. to 90° C. for five hours, and a reaction product including amide propyl betaine as a carboxamide derivative was obtained.

The solid concentration of the obtained reaction product was measured, and it was found to be 35.4% by weight. Also, the sodium chloride content was measured by means of silver nitrate titration; the sodium chloride concentration was 5.1% by weight, and the active ingredient concentration (concentration of amide propyl betaine in the reaction product) was 30.3% by weight. Furthermore, the reaction product was extracted by means of the following petroleum ether extraction method. After evaporation to dryness, the extract was diluted with 2-propanol. Then, a GC analysis was performed in the same manner as Example 1 to measure the amide ester content in the amide propyl betaine, and it was found to be 0.05% by weight.

[Petroleum Ether Extraction Method]

The petroleum ether extraction was performed according to the analysis methods of The Japanese Standards of Cosmetic Ingredients.

TABLE 2

|  | Example 5 | Example 6 | Example 7 | Comparative Example 3 | Comparative Example 4 |
| --- | --- | --- | --- | --- | --- |
| Carboxamide | Example 1 | Example 3 | Example 4 | Comparative Example 1 | Comparative Example 1 |
| Amide ester in carboxamide (% by weight) | 0.18 | 0.02 | 0.15 | 0.40 | 0.40 |
| Hydrogen peroxide/ carboxamide (molar ratio) | 1.05 | 1.05 | 1.05 | 1.05 | 1.05 |
| Amidoamine oxide concentration (% by weight) | 30 | 35 | 40 | 30 | 15 |
| Amide ester in amidoamine oxide aqueous solution (% by weight) | 0.05 | 0.006 | 0.04 | 0.11 | 0.06 |
| Appearance after preserving at 0° C. for 1 week | Transparent liquid | Transparent liquid | Transparent liquid | Clouded | Clouded |
| Low-temperature preservation stability | Good | Good | Good | NG | NG |

The results in Table 2 indicate that the content of the amide ester exceeding 0.05% by weight in an aqueous solution of 15% by weight to 40% by weight of amidoamine oxide precipitated the amide ester during low-temperature preservation and clouded the appearance but that the content of the amide ester of 0.05% by weight or less resulted in superior low-temperature stability.

Example 8

Preparation of Carboxamide Derivative

In a 1-Liter four-neck flask equipped with a stirrer, a thermometer and a reflux condenser, 150 g of lauric acid dimethylaminopropylamide prepared in Example 1 (molecular weight of 285, calculated based on the amine value, and First, a sample of 10 g was weighed and dissolved in a mixture of 100 mL of water and 100 mL of ethanol. The solution was transferred to a separating funnel, and extraction was performed three times, each with 50 mL of petroleum ether. The petroleum ether extract was combined, and the mixture was washed three times, each with 50 mL of water. Then, the petroleum ether was distilled off with an evaporator to obtain an evaporated and dried material.

Comparative Example 5

Preparation of Carboxamide Derivative

A reaction product including amide propyl betaine as a carboxamide derivative was obtained by performing a reaction in the same manner as Example 8 except that 150 g of lauric acid dimethylaminopropylamide prepared in Comparative Example 1 (molecular weight of 285, calculated based on the amine value, and amide ester quantity of 0.40% by weight) as carboxamide.

The solid concentration of the obtained reaction product was measured, and it was found to be 35.5% by weight. Also, the sodium chloride content was measured by means of silver nitrate titration; the sodium chloride concentration was 5.1% by weight, and the active ingredient concentration (concentration of amide propyl betaine in the reaction product) was 30.4% by weight. Furthermore, the reaction product was extracted by means of the petroleum ether extraction method. After evaporation to dryness, the extract was diluted with 2-propanol. Then, a GC analysis was performed in the same manner as Example 1 to measure the amide ester content in the amide propyl betaine, and it was found to be 0.11% by weight.

The results of Example 8 and Comparative Example 5 are shown in Table 3.

The amide propyl betaines as a carboxamide derivative prepared in Example 8 and Comparative Example 5 were preserved at 0° C. for one week, and the low-temperature stability after preservation was evaluated. The appearance of amide propyl betaine was visually observed for its transparency, and the low-temperature stability was rated as 'Good' or 'NG'. The results are shown in Table 3.

TABLE 3

|  | Example 8 | Comparative Example 5 |
|---|---|---|
| Carboxamide | Example 1 | Comparative Example 1 |
| Amide ester in carboxamide (% by weight) | 0.18 | 0.40 |
| Amide propyl betaine concentration (% by weight) | 30.3 | 30.4 |
| Amide ester in amide propyl betaine per petroleum ether extracted and dried material (% by weight) | 0.05 | 0.11 |
| Appearance after preserving at 0° C. for 1 week | Transparent liquid | Clouded |
| Low-temperature preservation stability | Good | NG |

The results in Table 3 indicate that, when the content of amide ester in carboxamide was 0.40% by weight, the content of amide ester in the amide propyl betaine prepared with the carboxamide was 0.11% by weight, resulting in the precipitation of the amide ester during low-temperature preservation but that when the content of amide ester in carboxamide was 0.18% by weight, the content of amide ester in the amide propyl betaine prepared with the carboxamide was as small as 0.05% by weight, resulting in superior low-temperature stability.

Example 9

Dishwashing Detergent Composition

As a detergent composition with a carboxamide derivative of the present invention, a dishwashing detergent composition was prepared by mixing the following: 10% by weight of amidoamine oxide prepared in Example 5; 15% by weight of sodium lauryl ether sulfate ($C_{12}$AESNa; manufactured by Lion Corp. with average number of EO moles added of 3); 10% by weight of $C_{12}$POE alkyl ether (manufactured by Lion Corp. with average number of EO moles added of 15); 5% by weight of $C_{12}$ fatty acid diethanol amide (manufactured by Lion Chemical Co., Ltd.); 1% by weight of PEG1000 (manufactured by Lion Chemical Co., Ltd.); 3% by weight of ethanol (manufactured by Kanto Chemical Co., Inc.); 1% by weight of sodium benzoate (manufactured by Kanto Chemical Co., Inc.); and 5% by weight of p-toluene sulfonic acid (manufactured by Kanto Chemical Co., Inc.). The pH of the obtained dishwashing detergent composition was adjusted to 6.6.

Comparative Example 6

Dishwashing Detergent Composition

As a detergent composition with a carboxamide derivative of the present invention, a dishwashing detergent composition was prepared by mixing the following: 10% by weight of amidoamine oxide prepared in Comparative Example 3; 15% by weight of sodium lauryl ether sulfate ($C_{12}$AESNa; manufactured by Lion Corp. with average number of EO moles added of 3); 10% by weight of $C_{12}$POE alkyl ether (manufactured by Lion Corp. with average number of EO moles added of 15); 5% by weight of $C_{12}$ fatty acid diethanol amide (manufactured by Lion Chemical Co., Ltd.); 1% by weight of PEG1000 (manufactured by Lion Chemical Co., Ltd.); 3% by weight of ethanol (manufactured by Kanto Chemical Co., Inc.); 1% by weight of sodium benzoate (manufactured by Kanto Chemical Co., Inc.); and 5% by weight of p-toluene sulfonic acid (manufactured by Kanto Chemical Co., Inc.). The pH of the obtained dishwashing detergent composition was adjusted to 6.6.

The dishwashing detergent compositions of Example 9 and Comparative Example 6 were tested and evaluated for their detergency, foaming and low-temperature stability as follows. The results are shown in Table 4.

<Detergency>

—Test Method—

A Tupperware of 10 cm×15 cm was uniformly coated with 1 g of beef tallow, and severely greasy hydrophobic soil was formed. Next, 38 g of water as well as 2 g of dishwashing detergent composition of Example 8 or Comparative Example 3 were put on dishwashing sponge of 11.5 cm×7.5 cm×3 cm, and the sponge was squeezed by hand for a few times. Then, the greasy Tupperware was cleansed at 25° C. in the same manner as routine household use. After cleansing, it was rinsed well with water.

—Evaluation Method—

After cleansing, the greased surface of the Tupperware was touched by hand, and a sensory evaluation was performed for the feel based on the following criteria.

[Evaluation Criteria]

A: The Tupperware was completely squeaky clean, and there was no greasy part due to residual oil.

B: The flat surface of the Tupperware was squeaky clean and had no residual oil, but edges and corners remained slightly greasy.

C: The whole Tupperware was greasy, and it was clear that the oil remained.

<Foaming>

—Test Method—

On dishwashing sponge of 11.5 cm×7.5 cm×3 cm, 38 g of water as well as 2 g of dishwashing detergent composition of Example 8 or Comparative Example 3 were put, and the sponge was squeezed by hand for a few times.

—Evaluation Method—

The foaming of the dishwashing detergent composition on the dishwashing sponge was visually observed after it was squeezed by hand, and a sensory evaluation was performed based on the following criteria.

[Evaluation Criteria]
A: Foaming well with good foam quality
B: Somewhat foaming
C: Hardly foaming <Low-Temperature Stability>

—Test Method—

The dishwashing detergent composition of Example 9 and Comparative Example 6 were respectively filled in 100-mL glass bottles. These were frozen by preserving them in a thermostat at −20° C. for one day, and then they were defrosted and restored in a thermostat at 0° C. for one day. This series of operations was considered as one cycle, and this cycle was repeated three times.

—Evaluation Method—

After the completion of three cycles, the appearance of each dishwashing detergent composition was visually observed at 0° C., and sensory evaluation was performed based on the following criteria.

[Evaluation Criteria]
A: Uniformly transparent
C: Cloudy or with precipitation

TABLE 4

|  | Example 9 | Comparative Example 6 |
| --- | --- | --- |
| Amidoamine oxide | Example 5 | Comparative Example 3 |
|  | 10% by weight | 10% by weight |
| $C_{12}$AESNa | 15% by weight | 15% by weight |
| (average number of moles added: 3) |  |  |
| $C_{12}$POE alkyl ether | 10% by weight | 10% by weight |
| (average number of moles added: 15) |  |  |
| $C_{12}$ fatty acid diethanol amide | 5% by weight | 5% by weight |
| PEG1000 | 3% by weight | 3% by weight |
| Ethanol | 3% by weight | 3% by weight |
| Sodium benzoate | 1% by weight | 1% by weight |
| p-Toluene sulfonic acid | 5% by weight | 5% by weight |
| Purified water | Balance | balance |
| pH | 6.6 | 6.6 |
| Detergency | A | A |
| Forming | A | A |
| Low-temperature stability | A | C |

The results in Table 4 indicate that the dishwashing detergent composition of Example 9 which includes the amidoamine oxide prepared in Example 5 having low content of amide ester yielded superior detergency, foaming and low-temperature stability. On the other hand, the dishwashing detergent composition of Comparative Example 6 which includes the amidoamine oxide prepared in Comparative Example 3 having high content of amide ester yielded inferior low-temperature stability.

Example 10

Hair Shampoo

As a detergent composition with a carboxamide derivative of the present invention, a shampoo as a detergent composition for hair was prepared by mixing the following: 20% by weight of amidoamine oxide prepared in Example 5; 10% by weight of sodium lauryl ether sulfate (Cl$_2$AESNa; manufactured by Lion Corp. with average number of EO moles added of 3); 3% by weight of coconut fatty acid diethanol amide (manufactured by Lion Chemical Co., Ltd.); 20% by weight of lauryl acid amide propyl betaine liquid (manufactured by Lion Corp.); 2.0% by weight of cationized cellulose (manufactured by Lion Corp.); 2.5% by weight of ethylene glycol distearate (manufactured by Ipposha Oil Industries Co., Ltd.); and 0.1% by weight of fragrance. The pH of the obtained hair shampoo was adjusted to 6.0.

Comparative Example 7

Hair Shampoo

A hair shampoo as a detergent composition for hair was prepared in the same manner as Example 10 except that the amidoamine oxide prepared in Comparative Example 3 was used in Example 10.

The following test was performed on the hair shampoos of Example 10 and Comparative Example 7, and they were evaluated for foam quality and low-temperature stability. The results are shown in Table 5.

<Foam Quality>

The hair shampoos of Example 10 and Comparative Example 7 were diluted such that the surfactant content was reduced to 5% by weight, and hair was shampooed with 5 mL of the diluted shampoos. At this point, sensory evaluations were performed for the foam quality based on the following criteria.

[Evaluation Criteria]
A: Creamy
B: Somewhat creamy
C: Not creamy

<Low-Temperature Stability>

The hair shampoos of Example 10 and Comparative Example 7 were respectively filled in 100-mL glass bottles. These were frozen by preserving them in a thermostat at −20° C. for one day, and then they were defrosted and restored in a thermostat at 0° C. for one day. This series of operations was considered as one cycle, and this cycle was repeated three times. After the completion of three cycles, the appearance of each hair shampoo was visually observed at 0° C., and sensory evaluation was performed based on the following criteria.

[Evaluation Criteria]
A: Uniformly transparent
C: Cloudy or with precipitation

TABLE 5

|  | Example 10 | Comparative Example 7 |
| --- | --- | --- |
| Amidoamine oxide | Example 5 | Comparative Example 3 |
|  | 10% by weight | 10% by weight |
| $C_{12}$AESNa | 10% by weight | 10% by weight |
| (average number of moles added: 3) |  |  |
| Coconut fatty acid diethanol amide | 5% by weight | 5% by weight |
| Lauryl acid amide propyl betaine | 15% by weight | 15% by weight |
| Cationized cellulose | 2% by weight | 2% by weight |
| Ethylene glycol distearate | 2.5% by weight | 2.5% by weight |
| Fragrance | 0.1% by weight | 0.1% by weight |
| Purified water | Balance | Balance |

TABLE 5-continued

|  | Example 10 | Comparative Example 7 |
|---|---|---|
| pH | 6.0 | 6.0 |
| Foam quality | A | A |
| Low-temperature stability | A | C |

The results in Table 5 indicate that the hair shampoo of Example 10 which included the amidoamine oxide prepared in Example 5 having low content of amide ester yielded superior foam quality and low-temperature stability. On the other hand, the shampoo of Comparative Example 7 which includes the amidoamine oxide prepared in Comparative Example 3 having high content of amide ester yielded inferior low-temperature stability.

INDUSTRIAL APPLICABILITY

A carboxamide derivative produced using a method for producing a carboxamide derivative of the present invention and using carboxamide produced with a method for producing with a method for producing carboxamide of the present invention yields low content of amide ester and superior low-temperature stability; therefore, it is favorably used for a detergent composition. Also, a detergent composition including a carboxamide derivative of the present invention has favorable low-temperature stability and superior detergency and foaming power. Therefore, it may be favorably used for various kinds of detergents, especially hair shampoo, body shampoo, face wash, hair treatment, dishwashing detergent and various household detergents.

What is claimed is:

1. A method for producing a carboxamide derivative comprising:

synthesizing a carboxamide by reacting, no presence a catalyst, a fatty acid ester represented by General Formula (1) below with a diamine represented by General Formula (2) below at a molar ratio of the diamine to the fatty acid ester of 1.20 to 1.60; and producing a carboxamide derivative by reacting the carboxamide and hydrogen peroxide, wherein the carboxamide comprises 0.02% by weight to 0.18% by weight of amide ester represented by General Formula (3) below; and the carboxamide derivative is represented by General Formula (4) below:

$R^1$—COOR      General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

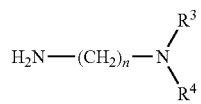

General Formula (2)

wherein, in General Formula (2) above, $R^3$ and $R^4$ are the same or different and represent an alkyl group having a carbon number of one to four; and n represents an integer of two to four;

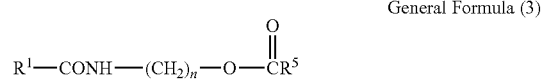

General Formula (3)

wherein, in General Formula (3) above, $R^1$ and $R^5$ represent any one of a straight-chain or branched-chain alkyl group, alkenyl group and hydroxyalkyl group having a carbon number of five to 12; and n represents an integer of two to four, and

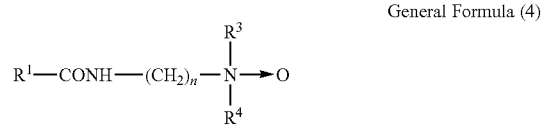

General Formula (4)

wherein, in General Formula (4), $R^1$ represents any one of a straight-chain or branched-chain alkyl group, alkenyl group and hydroxyalkyl group having a carbon number of five to 12; $R^3$ and $R^4$ are the same or different, representing an alkyl group having a carbon number of one to four; and n represents an integer of two to four.

2. A method for producing a carboxamide derivative comprising:

synthesizing a carboxamide by reacting, under no presence of a catalyst, a fatty acid ester represented by General Formula (1) below with a diamine represented by General Formula (2) below at a molar ratio of the diamine to the fatty acid ester of 1.20 to 1.60; and producing a carboxamide derivative by reacting the carboxamide and any one of monohaloalkylcarboxylic acid represented by Structural Formula (5) below and a salt thereof, wherein the carboxamide comprises 0.02% by weight to 0.18% by weight of amide ester represented by General Formula (3) below; and the carboxamide derivative represented by General Formula (6) below:

$R^1$—COOR      General Formula (1)

wherein, in General Formula (1) above, $R^1$ represents any one of a straight-chain or branched-chain alkyl group, alkenyl group and hydroxyalkyl group having a carbon number of five to 12; and $R^2$ represents a straight-chain or branched-chain alkyl group having a carbon number of one to four;

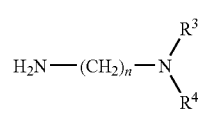

General Formula (2)

wherein, in General Formula (2) above, $R^3$ and $R^4$ are the same or different and represent an alkyl group having a carbon number of one to four; and n represents an integer of two to four;

General Formula (3)

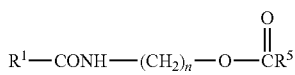

wherein, in General Formula (3) above, $R^1$ and $R^5$ represent any one of a straight-chain or branched-chain alkyl group, alkenyl group and hydroxyalkyl group having a carbon number of five to 12; and n represents an integer of two to four;

$YR^6COOZ$      General Formula (5)

wherein, in General Formula (5), Y represents a halogen atom; $R^6$ represents a straight-chain or branched-chain alkylene group having a carbon number of one to three; and Z represents any one of a hydrogen atom and an alkali metal atom; and General Formula (6)

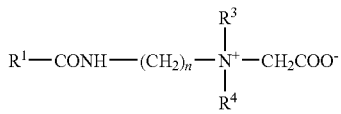

wherein, in General Formula (6), $R^1$ represents any one of a straight-chain or branched-chain alkyl group, alkenyl group and hydroxyalkyl group having a carbon number of five to 12; $R^3$ and $R^4$ are the same or different, representing an alkyl group having a carbon number of one to four; and n represents an integer of two to four.

3. The method for producing carboxamide derivative according to claim 1, wherein the reaction temperature for synthesizing carboxamide is 190° C. to 200° C.

4. The method for producing carboxamide derivative according to claim 2, wherein the reaction temperature for synthesizing carboxamide is 190° C. to 200° C.

5. The method for producing a carboxamide derivative according to claim 1, wherein the content of amide ester represented by General Formula (3) below in the carboxamide derivative is 0.05% by weight or less:

General Formula (3)

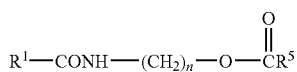

wherein, in General Formula (3) above, $R^1$ and $R^5$ represent any one of a straight-chain or branched-chain alkyl group, alkenyl group and hydroxyalkyl group having a carbon number of five to 12; and n represents an integer of two to four.

6. The method for producing a carboxamide derivative according to claim 2, wherein the content of amide ester represented by General Formula (3) below in the carboxamide derivative is 0.05% by weight or less:

General Formula (3)

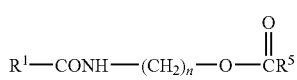

wherein, in General Formula (3) above, $R^1$ and $R^5$ represent any one of a straight-chain or branched-chain alkyl group, alkenyl group and hydroxyalkyl group having a carbon number of five to 12; and n represents an integer of two to four.

* * * * *